(12) United States Patent
Schütze

(10) Patent No.: US 8,293,497 B2
(45) Date of Patent: Oct. 23, 2012

(54) MICRODISSECTION METHOD AND MICRODISSECTION SYSTEM

(75) Inventor: Karin Schütze, Tutzing (DE)

(73) Assignee: P.A.L.M. Microlaser Technologies GmbH (DE)

( * ) Notice: Subject to any disclaimer, the term of this patent is extended or adjusted under 35 U.S.C. 154(b) by 1142 days.

(21) Appl. No.: 12/168,339

(22) Filed: Jul. 7, 2008

(65) Prior Publication Data

US 2008/0269637 A1    Oct. 30, 2008

Related U.S. Application Data

(63) Continuation of application No. PCT/EP2006/012316, filed on Dec. 20, 2006.

(30) Foreign Application Priority Data

Jan. 5, 2006    (DE) .......................... 10 2006 000 934

(51) Int. Cl.
  *C12Q 1/24*    (2006.01)
  *G01N 1/04*    (2006.01)
  *G01N 1/22*    (2006.01)
  *G01N 21/00*    (2006.01)
  *H01J 49/04*    (2006.01)

(52) U.S. Cl. ....... 435/40.52; 435/30; 436/173; 250/286; 600/564

(58) Field of Classification Search ........................ None
See application file for complete search history.

(56) References Cited

U.S. PATENT DOCUMENTS 5,998,129 A * 12/1999 Schutze et al. .................. 435/4

FOREIGN PATENT DOCUMENTS

| | | | |
|---|---|---|---|
| DE | 100 15 157 A1 | | 10/2001 |
| DE | 10015157 A1 | * | 10/2001 |
| EP | 1 367 380 A1 | | 12/2003 |
| EP | 1367380 A1 | * | 12/2003 |
| WO | 02/10751 A2 | | 2/2002 |
| WO | WO 0210751 A2 | * | 2/2002 |
| WO | 2004/045768 A1 | | 6/2004 |
| WO | WO 2004045768 A1 | * | 6/2004 |
| WO | 2005/107949 A1 | | 11/2005 |
| WO | WO 2005107949 A1 | * | 11/2005 |
| WO | 2005/114135 A1 | | 12/2005 |
| WO | WO 2005114135 A1 | * | 12/2005 |
| WO | 2007/076934 A1 | | 7/2007 |
| WO | WO 2007076934 A1 | * | 7/2007 |

OTHER PUBLICATIONS

Carl,D; Hoink,a;von Bally,G;Denz, C "Digital Holographic Microscope for the Analysis of Living Cells", DGaO-Proceedings 2004, 4 pages.*

"Microdissection: A method developed to investigate mechanisms involved in transmissible spongiform encephalopathy pathogensis" by Barr, J.B., et al., BMC Infectious Diseases, Mar. 2004, 4 (8), 9 pages.

"Evolution of intratumoral genetic heterogeneity during colorectal cancer progression" by Losi, L., et al., Carcinogensis, 2004, 26 (5), pp. 916-922.

"Holographic interferometric microscopy systems for the application on biological samples" by Kemper, B., et al., Proc. of SPIE, 2004, vol. 5457, pp. 581-588.

* cited by examiner

*Primary Examiner* — Chris R Tate
*Assistant Examiner* — Aaron J Kosar
(74) *Attorney, Agent, or Firm* — Mayback & Hoffman, P.A.; Gregory L. Mayback; Rebecca A Tie

(57) ABSTRACT

In a microdissection method and a microdissection system, first and second objects are transported from a preparation to first and second collection devices, respectively, so that a position of the second collection device relative to the first collection device substantially corresponds to a position of the second object relative to the first object in the preparation.

16 Claims, 2 Drawing Sheets

MICRODISSECTION METHOD AND MICRODISSECTION SYSTEM

CROSS-REFERENCE TO RELATED APPLICATION

This is a continuing application, under 35 U.S.C. §120, of copending international application No. PCT/EP2006/012316, filed Dec. 20, 2006, which designated the United States and was not published in English; this application also claims the priority, under 35 U.S.C. §119, of German patent application No. DE 10 2006 000 934.7, filed Jan. 5, 2006; the prior applications are herewith incorporated by reference in their entirety.

BACKGROUND OF THE INVENTION

1. Field Of The Invention

The present invention relates to a laser microdissection method and a laser microdissection system for separating and obtaining objects of a preparation, in particular a biological preparation. The present invention relates in particular to a laser microdissection method and a laser microdissection system for obtaining objects of a spatially inhomogeneous preparation.

A conventional laser microdissection system in the name of the Applicant is known, for example, from WO 97/29355 A or from WO 01/73398 A. This laser microdissection system allows computer-assisted selection of individual biological or non-biological objects that are disposed on a planar carrier to be carried out, and it allows the objects to be processed by a laser beam. For example, the object can be transported to one or more collection devices by being processed with the laser beam. A plurality of transport processes, induced directly or indirectly by the laser beam, are possible and these are described in the cited documents. For example, a selected object may be fully or partially separated from the surrounding preparation by the laser beam, and may thus be released. The released object may then be accelerated or "catapulted" from the carrier to a collection device by a laser-induced transport process with the aid of a laser shot, which is directed onto the object. The object may also be released so that it is still connected to the surrounding preparation by a residual web, in which case the laser shot may be used both to cut through the residual web and to catapult the object to the collection device.

In principle, the laser-induced transport process may be carried out even without the respectively selected object being released beforehand, if the force acting on the object is sufficient both for detaching the object from the preparation and also for accelerating it to the collection device.

Laser microdissection systems make it possible to separate, sort and obtain both biological and non-biological objects. In particular, laser microdissection allows contact-less separation of biological objects, for example, individual cells, from a preparation to be performed. Because the biological objects are not damaged or compromised by the separation and/or catapulting process, after the separation, they are available for further studies or further cultivation.

For example, tumor cells may be separated from healthy cells of a tissue section and subsequently studied. If a plurality of collection devices are provided for separate objects, for example, different cells, then the objects may be catapulted into different collection devices according to their type and thus sorted.

As objects of the same type, for example, tumor cells, may have different properties, there is a need in the art for microdissection methods and microdissection systems that make it possible for objects separated from the preparation to be sorted not only according to an object type, but also according to other criteria.

2. Summary Of The Invention

With the foregoing and other objects in view, there is provided, in accordance with the invention, a microdissection method including the steps of providing a preparation, providing a plurality of collection devices for collecting an object detached from the preparation, the plurality of collection devices having a predefined spatial configuration relative to one another, transporting a first object of the preparation by laser irradiation to a first collection device and transporting a second object of the preparation by laser irradiation to a second collection device. The first object and/or the second object are transported so that a position of the second collection device relative to the first collection device corresponds to a position of the second object relative to the first object in the preparation. In this context, correspondence between the relative position of the collection device and the relative position of the objects in the preparation does not necessarily mean that the relative positions are identical. Rather, the relative position of the collection device may for example be equal to the relative position of the objects increased by a scaling factor. Due to the fact that the relative position of the objects to be transported to the first and second collection devices, respectively, corresponds to the relative position of the collection device, during subsequent studies of the objects detached from the preparation it is possible to obtain information about the position of the first and second objects in the preparation before detachment, based upon the collection device to which the first and second objects are respectively allocated. This allows spatially resolved studies of the preparation to be performed.

With the objects of the invention in view, there is also provided a method for performing microdissection, including the steps of providing a preparation, providing a plurality of means for collecting objects detached from the preparation, the plurality having a predefined spatial configuration relative to one another, and transporting a first object of the preparation to a first collection means and transporting a second object of the preparation different from the first object to a second collection means, respectively, by laser irradiation, at least one of the first and second objects being transported respectively to the first and second collection means so that a position of the second collection means relative to the first collection means corresponds to a position of the second object relative to the first object in the preparation.

With the objects of the invention in view, there is also provided a microdissection system including a holder operable for containing a preparation, a support for supporting a first collection device and a second collection device, which are respectively adapted for collecting an object detached from the preparation, the first and second collection devices having a predefined spatial configuration relative to one another, a laser light source for generating a laser beam to accelerate objects of the preparation, and a controller coupled to the laser light source and adapted to control the laser light source so that the first object and/or the second object are transported respectively to the first collection device and to the second collection device, such that a position of the second collection device relative to the first collection device corresponds to a position of the second object relative to the first object in the preparation.

With the objects of the invention in view, there is also provided a microdissection system, including means for holding a preparation, support means for supporting first and second collection means, the first and second collection means being respectively operable for collecting an object detached from the preparation, the first and second collection means having a predefined spatial configuration relative to one another, a laser-beam-generating light source operable for transporting first and second objects of the preparation respectively to the first and the second collection means, and control means operable for controlling the light source to respectively transport at least one of the first and second objects to the first and second collection means such that a position of the second collection means relative to the first collection means corresponds to a position of the second object in the preparation relative to the first object in the preparation.

Exemplary embodiments of the invention will be described below with reference to the drawings.

Correspondence between the relative position of the objects and the relative position of the collection devices may be achieved by selecting the objects to be accelerated according to the relative position of the collection devices. In this context, the selection of an object to be detached from the preparation and accelerated by laser irradiation refers to a process that precedes the actual transport process and comprises, in particular, the establishment of an edge of the object to be detached. When the object is released, this edge of the object to be detached generally defines a cutting line along which the object is detached by laser irradiation from the surrounding preparation.

The first and second objects may be transported so that the position of the second collection device relative to the first collection device is substantially equal to the position of the second object relative to the first object in the preparation, multiplied by a scaling factor. The scaling factor may be determined by a characteristic spacing of objects to be detached from the preparation and a characteristic spacing of the collection devices. Because the relative position of the collection devices has a simple relationship with the relative position of the corresponding objects on the preparation, even after a laser-induced transport process from the preparation to the collection devices, it is then possible to obtain information about the original relative location, in the preparation, of the objects to be transported to the collection devices. It should be borne in mind that the first and second objects will generally be two-dimensionally or three-dimensionally extended objects. The term "position" is in this case to be understood as an abbreviation for the position of a characteristic point of the two-dimensionally or three-dimensionally extended object, for example, as the position of the surface midpoint or the volume midpoint of the corresponding object.

The method according to the various embodiments of the invention may readily be extended to an arbitrary plurality of objects. In particular, if a third collection device is available, then a third object of the preparation may be transported to the third collection device by laser irradiation, in which case the third object is, again, selected so that the position of the third collection device relative to the first collection device is substantially equal to the position of the third object relative to the first object on the preparation, multiplied by the scaling factor. The method may correspondingly be extended to further objects of the preparation. The effect achieved by this is that the morphology of the preparation is reflected in the distribution of the objects detached from it in the various collection devices, into which the objects have been transported by laser irradiation. This generates, so to speak, an image of the original preparation magnified by the scaling factor in the collection devices, i.e., the objects of the preparation are catapulted out of it while preserving the pattern.

The method according to the various embodiments is adapted for extensive automation. In particular, an overview image of the preparation may be generated by a suitable camera, for example, a CCD camera, and a preparation region may be selected based upon the overview image. The selection of the preparation region may be carried out automatically with computer assistance or by user selection. The objects to be transported by laser irradiation may be selected subsequently fully automatically or semi-automatically. In particular, the edges of the objects to be detached from the preparation may be ascertained automatically as a function of the dimensions of the selected preparation region and the number of collection devices available, for example, in that cutting lines for detaching the objects are established with computer assistance. In one exemplary embodiment, the cutting lines define a regular grid so that, by laser irradiation, the preparation is cut along the grid lines and subsequently transferred in a grid array fashion to corresponding collection devices. The laser-induced transport of objects may also be extended to objects in a vicinity of the selected preparation region, especially if the geometrical shape of the selected preparation region differs from the configuration of collection devices. In such a case, optimal utilization of all available collection devices can be achieved with simultaneous pattern preservation. Not only the selection of objects to be transported to the collection devices, i.e., the division of the preparation into a certain number of aliquots, but also the transport induced by the laser irradiation may be carried out automatically and with computer assistance. For example, after the objects to be accelerated have been selected based upon the overview image, a laser light source and an adjustment device for the preparation may be controlled so that a movement of the preparation is induced relative to a laser beam and the object to be transported is released along its edge from the surrounding preparation.

The selection of the first and/or second object may include the steps of ascertaining a number of collection devices along an axis, which is defined by the first and the second collection devices, ascertaining a length of the preparation region in a direction parallel to the axis, and determining a position of the second object relative to the first object by multiplying the ratio of the length of the preparation region and the number of collection means by an integer. Particularly for the case of a regular configuration of collection devices, for example, the configuration of wells of a microtitre plate on the grid points of a grid line network, these steps constitute a simple method to determine the position of the second object based upon the first object and, thus, select the second object. In the case of a predetermined first object, for example, the position of the second object on the preparation may be ascertained from the number of collection devices along a given axis of the configuration of collection means as well as the extension of the preparation in the direction defined by this axis. The integer may be set to be equal to the number of collection devices disposed along the axis between the first and the second collection device plus 1. When a plurality of objects is transported to a plurality of collection devices, this selection makes it possible to fill the configuration of collection devices without leaving gaps.

Even though for many applications objects are selected so that they have approximately equal areas in a plane defined by the preparation, the selection of the objects to be transported may also comprise determining of a thickness of the preparation in the vicinity of the positions of the respective objects, in which case the objects are subsequently selected based upon the ascertained thickness. In accordance with another mode of the invention, a thickness of the preparation is ascertained respectively in a vicinity of the first and second objects and the first and second objects are selected so that an area of the first object and an area of the second object is set as a function of the thickness of the preparation respectively ascertained in the vicinity of the first and second objects. For example, an object may be selected so that its area in a plane defined by the preparation is approximately inversely proportional to the respectively ascertained thickness of the preparation at the object. Therefore, objects with approximately equal volumes may be selected and transported to the corresponding collection devices. The thickness determination may be carried out in any suitable way, for example, by image analysis, in particular, by digital holographic interferometry.

The laser-induced transport process from the preparation to the collection devices may also be carried out in a variety of ways in the method according to the various embodiments of the invention. In an exemplary embodiment, the beam direction of a laser beam, which is used to cut out and/or accelerate the objects, is fixed and the preparation and the collection devices are positioned relative to the laser beam. In another exemplary embodiment, the position of the preparation is fixed and the beam direction of the laser beam is varied. In particular, the collection devices will be positioned so that the corresponding collection device is positioned along a beam direction of the laser beam during the laser-induced transport process. Transporting of an object may, in particular, comprise cutting out and/or acceleration by laser irradiation. In particular, the laser-induced transport process may comprise laser-induced acceleration. In this way, the method may readily be carried out by using laser microdissection systems that operate in various operating modes.

The preparation may be a biological preparation, which may be solid or liquid. In the case of biological preparations, spatially resolved studies of the preparation are particularly desirable to be able to ascertain a variation in properties of objects of the same type, for example, tumor cells, as a function of a spatial position of the objects in the preparation.

The preparation may be a tissue section, for example, a histological tissue section, which comprises a tumor area. In such a case, the objects to be transported may be individual tumor cells or groups of tumor cells. By further study of the tumor cells that have been separated from the preparation by the method according to an embodiment of the invention and transported to the collection devices, information may, for example, be obtained about the various stages of the tumor cells, which may differ significantly according to their position. With the aid of the method according to an embodiment of the invention, a tumor can be studied in more detail and a better analysis can be carried out, for example, with respect to the aggression of tumor cells. Because the method can be substantially or fully automated, it also leads to a time saving in such studies of a tumor.

The preparation may also be cell culture, for example, a clone of a stem cell culture that, for more extensive processing, is intended to be divided into subcultures, for example, with equal volumes or equal cell numbers. By virtue of the method according to embodiments of the invention, clones can be simply, rapidly, and effectively divided into sub-clones or even individual cells, and transported in a laser-induced fashion to the desired collection means.

The preparation may also comprise a plant tissue section or plant cells.

The method according to the various embodiments of the invention may readily be adapted to a wide variety of different implementations of the collection devices. For example, the collection devices may be disposed on a collection device and may, for example, be the indentations (or wells) of a multi-plate having 6, 12, or 24 wells or a microtitre plate having 96, 384, or more wells. The plurality of collection devices may also be implemented by segments of a microchip or by glass plate segments coated with an adhesive or another suitable element. It is also feasible to provide a glass plate or another planar support that, for example, is coated at its surface with an adhesive, in which case different sections or regions of the surface of the glass plate or the planar support serve as collection devices. Particularly in the case of standardized collection devices, such as microtitre plates with a given number of wells, the number and relative position of collection devices may also be ascertained automatically, for example, by the method described in WO 04/045768 A in the name of the Applicant, and the laser-induced transport of objects from the preparation to the collection devices may thus be further automated.

Whereas in one exemplary embodiment a correspondence between the relative position of the objects to be transported and the relative position of the collection devices is achieved by determining the relative position of the collection devices and selecting the objects based thereon, the method according to embodiments of the invention may also be configured so that a plurality of objects to be transported are initially selected in the preparation and, then, a plurality of collection devices, to which the objects are respectively transported, are selected as a function of the relative positions of the objects.

A microdissection method according to one of the exemplary embodiments described above may furthermore be configured so that the pattern-preserving transfer of a selected preparation region can be carried out in various ways.

In one mode, the selected region is fully divided into a plurality of objects, which are subsequently transported according to one of the exemplary embodiments described above to a plurality of collection devices while preserving the pattern. In this case, the entire selected preparation region is available for further studies or further cultivation after transport to the collection devices. In particular, the selected preparation region may be subdivided into a plurality of rectangular objects that have the same area.

In another mode, a plurality of objects are selected in the selected preparation region so that the plurality of objects do not cover the entire preparation region. For example, objects may be selected with dimensions that are smaller than a characteristic spacing of the objects. The objects may, in particular, be selected with a rectangular or round shape, or any other desired shape. The selection of the area and/or shape of the objects may, for example, be carried out in a user-defined fashion. In particular, the objects may be selected so that they have approximately the same area and shape. Even though the entire selected preparation region is not in this case available in the collection devices for further studies or further cultivation, this method does allow spatially resolved study of the preparation region.

In yet another mode, a plurality of objects in the selected preparation region is selected so that the objects have approximately equal volumes or cell numbers. To this end, as described above, the thickness of the preparation is ascertained and a lateral size of the objects is determined as a function of the ascertained thickness. When selecting objects with approximately equal volumes or cell numbers, the objects may also be selected so that together they do not cover the entire selected preparation region. As an alternative, the lateral size and number of the objects to be transported may also be set as a function of a spatially varying thickness of the selected preparation region, so that the overall selected preparation region is subdivided into a plurality of objects with approximately equal volumes or cell numbers which are then transported to corresponding collection devices while preserving the pattern. In the latter case, the subdivision of the selected preparation region into a plurality of objects may also be carried out with computer assistance and automatically.

Not just one, but a plurality of pattern-preserving images of a preparation region can be generated with the method according to embodiments of the invention. To this end, in addition to the first and second collection devices, a plurality of secondary collection devices are provided. The plurality of secondary collection devices have a predefined spatial configuration relative to one another A first secondary object, which is in the vicinity of the first object in the preparation, is transported to the first secondary collection device and a second secondary object, which is in the vicinity of the second object in the preparation, is transported to the second secondary collection device, the transport in turn being carried out so that a position of the second secondary collection device relative to the first secondary collection device corresponds to a position of the second secondary object relative to the first secondary object in the preparation. With this method, objects of the preparation are transported to a plurality of collection devices and to a plurality of secondary collection devices while preserving the pattern. They are available for further studies or further cultivation both at the collection devices and at the secondary collection devices. The microdissection method may correspondingly be extended to further additional groups of collection devices and a correspondingly larger number of pattern-preserving images.

In practice, instead of selecting secondary objects to be transported respectively in a vicinity of the corresponding objects to be transported, a plurality of objects may be selected according to the microdissection method described above and subsequently subdivided respectively into a predetermined number of sub-objects, for example, four sub-objects. The first sub-objects of each of the objects are transported subsequently to corresponding collection devices of the plurality of collection devices, and the second sub-objects each of the objects are transported to corresponding secondary collection devices of the plurality of secondary objects, etc.

The exemplary embodiments of the microdissection method that have been described above may also be applied correspondingly to the transport of secondary objects to the corresponding secondary collection devices.

To this end, the microdissection system may comprise detector for ascertaining the position of the second collection device relative to the first collection device, the controller being adapted to induce a position change of the preparation using an adjustment device based on the position of the second collection device relative to the first collection device ascertained by the detector. The microdissection system according to embodiments of the invention may, therefore, be adapted to reposition the preparation in between laser-induced transport processes of objects to the first or second collection devices, so that the relative position of the first and second collection devices reflects the relative position of the first and second objects on the preparation. This makes it easier for objects, which have been transported to the collection means, to be spatially allocated to their original positions in the preparation.

In particular, the controller may be adapted to divide the position of the second collection device relative to the first collection device ascertained by the detector by a scaling factor so as to determine a position change value, and to control the adjustment device so that the position of the preparation is changed by the position change value. The scaling factor may be specified by a user or ascertained automatically by the control means. This configuration of the control means will readily allow pattern-preserving catapulting even for a multiplicity of objects from the preparation to the corresponding collection means.

The detection means may also be configured so that a relative position of collection devices, and possibly a total number of available collection devices, is ascertained automatically. As already mentioned above, this may for example be achieved by the system described in WO 04/045768 A, in which case, for example, a microtitre plate is identified with the aid of a barcode. This configuration of the detector allows even more extensive automation of the laser-induced transport process.

The microdissection method may furthermore comprise a thickness determination device coupled to the controller and are adapted to ascertain a thickness of the preparation in the vicinity of the first object and/or the second object. The controller is coupled to the adjustment device and/or the laser light source and is adapted to adjust a lateral size of the first and/or second object to be accelerated, as a function of the ascertained thickness of the preparation. A microdissection method so configured allows laser-induced transport of objects with approximately constant volumes and/or cell numbers.

Although the invention is illustrated and described herein as embodied in a laser microdissection method and a laser microdissection system for separating and obtaining objects of a preparation, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

BRIEF DESCRIPTION OF THE DRAWINGS

In the following, the invention will be described in more detail by exemplary embodiments and the corresponding figures. By schematic illustrations that are not true to scale, the figures show different exemplary embodiments of the invention.

DETAILED DESCRIPTION OF THE INVENTION

Herein various embodiment of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Figure 1:
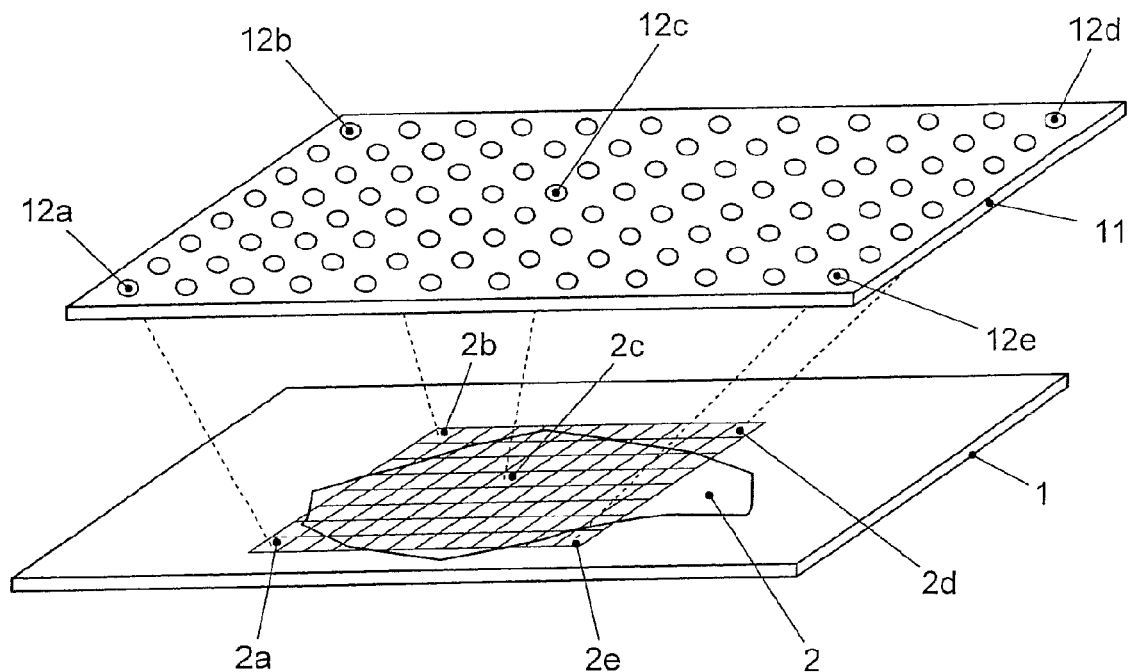
FIG. 1 is a fragmentary, perspective view of a basic principle of a microdissection method according to an exemplary embodiment of the invention.

Referring now to the figures of the drawings in detail and first, particularly to FIG. 1 thereof, there is shown the principle of a microdissection method according to one embodiment of the invention. A biological preparation 2, for example, a histological tissue section, is applied on a carrier 1, for example, a polymer sheet or a glass carrier possibly with an additional laser light-absorbing sheet disposed thereon. A microtitre plate 11 comprises a plurality of wells 12A-E.

Objects 2a-e are transported by laser-induced transport processes from the biological preparation 2 to the wells 12a-e. As represented schematically by the dashed lines joining the objects 2a-e to the corresponding wells 12a-e, this transport is carried out so that a spatial configuration of the wells 12a-e corresponds to the spatial configuration of the objects 2a-e on the carrier 1, even though the relative positions are increased by a scaling factor due to the larger distances between the corresponding wells 12a-e, compared with the distances between the objects 2a-e.

After the objects 2a-e and, optionally, the schematically indicated further objects of the preparation (which are not provided with reference signs), have been transported by laser irradiation from the carrier 1 to the corresponding wells of the microtitre plate 11, the geometrical configuration of the objects collected in the wells of the microtitre plate 11 corresponds to the original geometrical configuration of the objects on the carrier, increased by the scaling factor. Information about the spatial configuration of the objects in the original preparation may, therefore, readily be obtained during further studies of the objects collected in the individual wells.

If the biological preparation 2 is, for example, a histological tissue section that comprises a tumor area, then, during further studies of the objects transported to the microtitre plate 11, each of the objects typically being individual cells or a plurality of cells, information can thus be obtained about the various stages of tumor cells, which may differ significantly according to their position. For instance, peripheral cells are usually more aggressive and susceptible to metastasis whereas centrally placed cells sometimes even die off. With the aid of the method outlined above, a tumor can, therefore, be studied in more detail and an improved analysis of the aggression of the tumor can, therefore, be carried out.

It should be noted that in the exemplary embodiment shown in FIG. 1, a segment of the preparation is fully divided into fields that define the objects to be transported and the fields (and therefore the corresponding segment of the preparation) is/are fully transported to the collection device.

The microdissection method will be explained in more detail below with reference to FIGS. 2a to 2c.

Figure 2A:
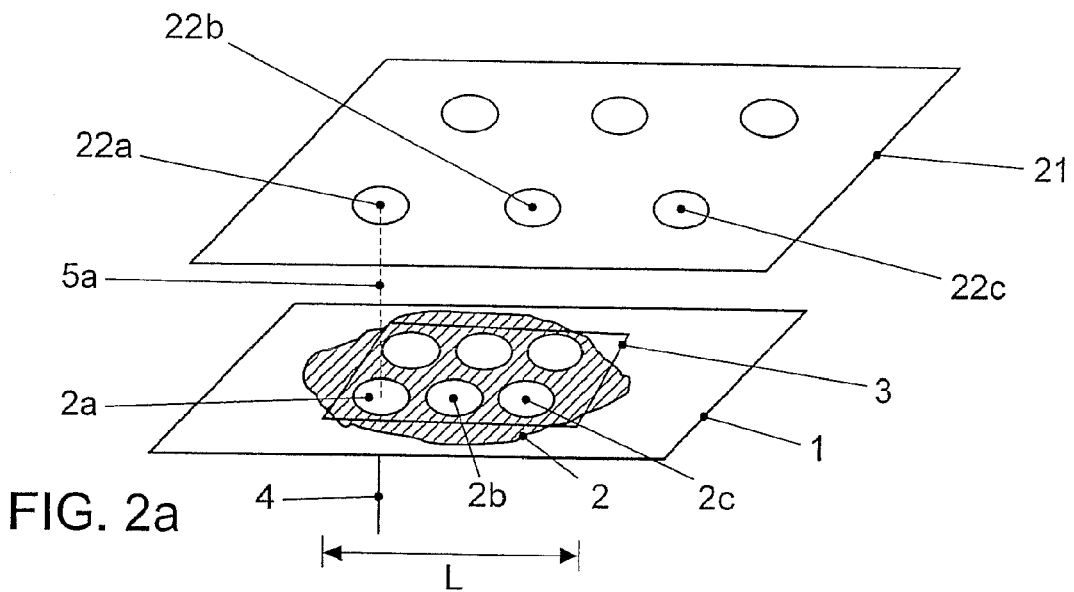
FIGS. 2a, 2b, and 2c are fragmentary perspective view of diagrammatic representations of steps of a microdissection method according to an exemplary embodiment of the invention.
Figure 2B:
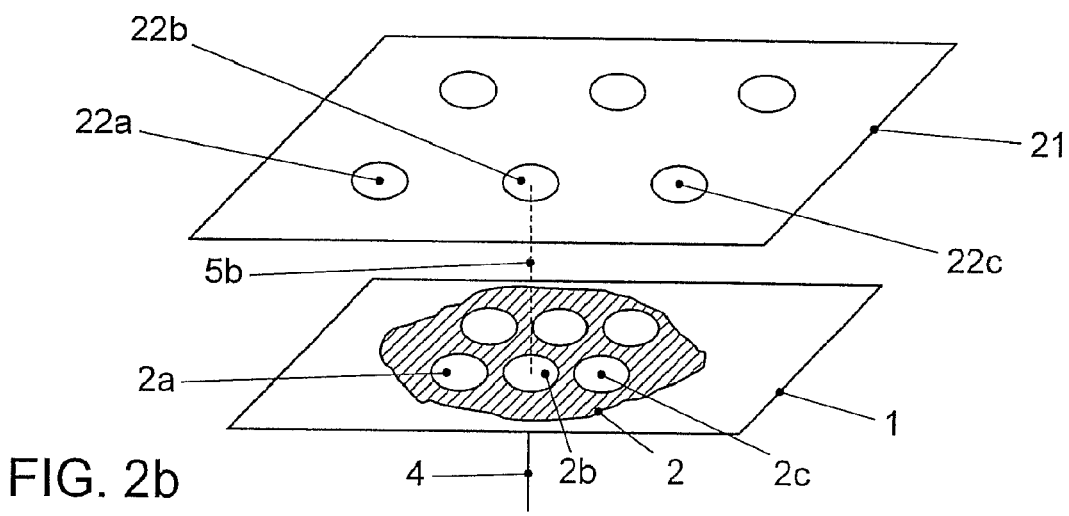
Figure 2C:
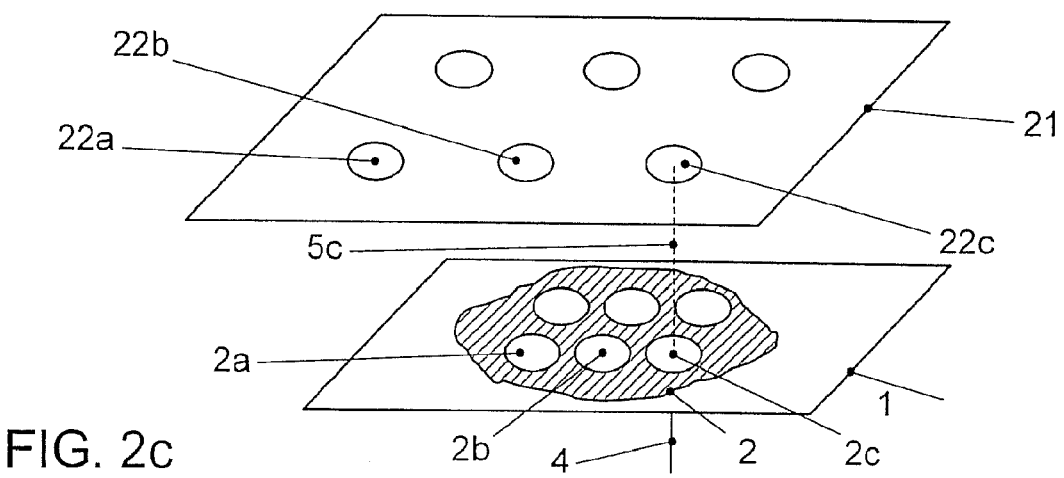

The collection device of FIGS. 2a, 2b and 2c is a 6-well plate 21, which has a plurality of wells 22a-c. The number and configuration of the wells may either be input by a user into a computer of the microdissection system or ascertained automatically by the microdissection system, for example, using information applied on the 6-well plate 21 in the form of a barcode.

Based upon an overview image of the biological preparation 2, which has been recorded by a suitable camera and is displayed on a monitor coupled to the computer, a preparation region is demarcated with a contour line 3 either by user input or automatically. Based on the overview image and the information about the number and configuration of the wells, the computer automatically ascertains the position of the surface midpoints of the objects 2a-c that are intended to be transported from the preparation to the 6-well plate 21. To this end, starting with the number of wells disposed along the axis defined by the wells 22a and 22b, in this case, three of them, and the extension L of the preparation in a direction parallel to the axis, a distance between neighboring objects 2a and 2b or 2b and 2c is calculated as L/3. Similarly, for each of the objects to be transported, the position of the surface midpoint relative to that of the first object 2a may be calculated based upon the dimensions of the preparation region and the number and configuration of wells on the 6-well plate 21. By these steps, a position of the surface midpoints of the objects 2a-c is ascertained. The information about a lateral size of the object, which is furthermore required to select the object, may be established either in a user-defined fashion so that it is the same for all objects, or individually for all objects, or automatically.

In the exemplary embodiment shown in FIG. 2, the objects 2a-c have a size that is smaller than the characteristic distance between the objects. In this exemplary embodiment, therefore, not all of the selected preparation region is transported to the collection device.

As may be seen from FIG. 2a, the position of the second object 2b relative to the first object 2a is equal to the position of the second collection device 22b relative to the first collection device 22a, divided by a scaling factor, and the position of the third object 2c relative to the first object 2a is equal to the position of the third collection device 22c relative to the first collection device 22a divided by the same scaling factor. In the example represented, the scaling factor is determined by the spacing of the wells, the number of wells and the length L of the selected preparation region.

The scaling factor may, in general, depend on the spatial direction, particularly if the geometrical shape of the selected preparation region differs substantially from the geometrical shape of the configuration of wells. In this case, the relative positions of objects that are adjacent in the corresponding spatial direction may be ascertained separately for each spatial direction in the manner described above.

After selection of the objects 2a-c to be transported by laser irradiation, the computer drives a motorized microscope stage on which the carrier 1 is disposed, so that the carrier 1 with the preparation 2 is moved relative to a laser beam 4 and the laser beam 4 travels along the edge of a selected object and, therefore, releases the object. In addition, a support device for the 6-well plate 21 is driven so that the well corresponding to the cut-out object is positioned along the beam direction of the laser beam 4. This situation is represented schematically in FIG. 2a for the object 2a. After the object 2a has been cut out, the object 2a is accelerated by a laser shot to the well 22a along the trajectory 5a. The laser shot may, in this case, be directed at the surface midpoint of the object.

The cutting-out and catapulting is subsequently repeated for the objects 2b and 2c by driving the microscope stage and the support device of the 6-well plate in a corresponding fashion, as shown schematically in FIGS. 2b and 2c.

Naturally, numerous modifications may be made to the method represented merely schematically with the aid of FIGS. 2a to 2c. For example, the objects 2a-c need not necessarily be isolated circular objects. Rather, the objects may have any shape and, as shown in FIG. 1, may adjoin one another. In particular, as likewise shown in FIG. 1, a preparation region may be fully divided into a multiplicity of fields that are then transported successively to corresponding wells.

Figure 3:
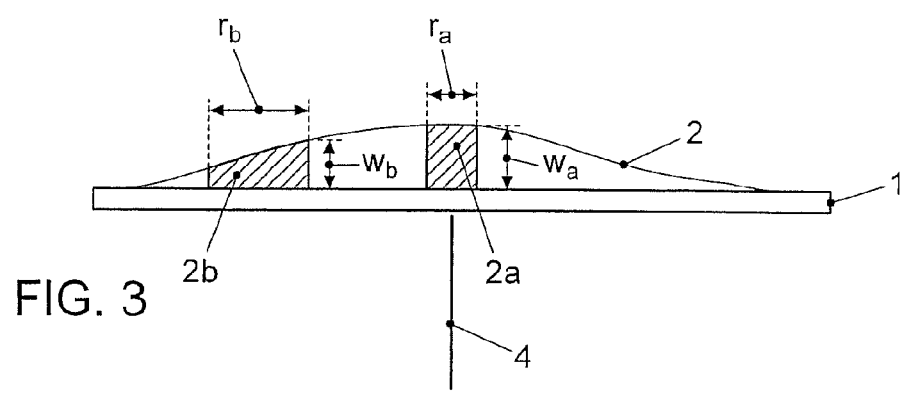
FIG. 3 is a fragmentary, side elevational view of a diagrammatic representation for explaining steps of a microdissection method according to another exemplary embodiment of the invention.

A microdissection method according to another exemplary embodiment of the invention will be described below with reference to FIG. 3. According to the microdissection method explained with reference to the schematic representations of FIG. 1 and FIG. 2, objects that have approximately constant or at least comparable areas are selected. In other applications, it may, however, be desirable or necessary to select objects with a comparable cell number or comparable volume.

To this end, after having determined the positions of the objects 2a-c according to the method described above, a lateral size of the objects may be set as a function of the thickness of the preparation at the respective objects, so that objects with an approximately constant volume are selected and transported to the collection device. To this end, a thickness determination device is provided, for example, in the form of a digital holographic interferometer, which determines the thickness $w_a$, $w_b$ of the preparation in the vicinity of the corresponding objects 2a, 2b. Based upon the thicknesses $w_a$, $w_b$, the computer then calculates the lateral dimensions $r_a$, $r_b$ of the corresponding objects in the plane of the preparation. If, in particular, it is necessary to transport objects with comparable volumes to the wells, then the lateral dimension of the objects 2a, 2b will be selected so that the area of the objects in the plane of the preparation is approximately inversely proportional to the corresponding thicknesses.

Such thickness-dependent selection of objects may, in particular, be employed in stem cell research. A stem cell culture often gives rise to clones that should be divided into subcultures for more extensive processing or study. A particular number of cells is required per sub-clone, for example, at least 50, so that the sub-clone can continue to grow. The method described above allows the cell number in selected sub-clones to be adjusted automatically.

It should be noted that although each of the exemplary embodiments above presents only one microtitre plate 11, or one 6-well plate 21, respectively with a plurality of collection devices, a plurality of such microtitre plates or multi-well plates may also be provided to collect objects. In such a case, a plurality of pattern-preserving images of the preparation may also be generated.

Referring to FIG. 1, for example, each of the fields 2a-e, i.e., each of the objects, may be divided into a plurality of sub-objects and each of the sub-objects may be released correspondingly. A first sub-object of the object 2a will, then, be transported to the well 12a of the microtitre plate 11, while a second sub-object of the object 2a will be transported to a correspondingly disposed well of a secondary microtitre plate (not illustrated) that is identical to the microtitre plate 11. The sub-objects of the other objects will be transported accordingly to the corresponding wells of the microtitre plate and the secondary microtitre plate (not shown). This means that the first sub-objects are transported to the collection device like the objects in the method described above, and the second sub-objects are transported as secondary objects to secondary collection device, this transport, in turn, being carried out according to the method described above. This modification of the method described above may readily be extended to an even larger number of microtitre plates.

The microdissection method and microdissection system according to the various embodiments of the invention may be used for studying any desired preparations, in particular, biological preparations. In particular, the microdissection method and microdissection system according to embodiments of the invention may be used for studying preparations for which spatially resolved study of the preparation is desired. The microdissection method may be used in both erect and inverse microscopes.

I claim:
1. A method for performing microdissection, the method comprising:
   a. providing a sample preparation;
   b. providing a plurality of object collection devices for collecting objects detachable from the sample preparation, the plurality of object collection devices positioned in a spatial configuration relative to one another and a distance from the sample preparation sufficient for spatial and selective collection of a plurality of the objects when the objects are detached from the sample preparation; and
   c. subjecting the sample preparation to laser irradiation thereby detaching and transporting:
      i. at least one first object from the sample preparation to a first object collection device, and
      ii. at least one second object from the preparation different from the first object to a second object collection device,
   wherein the at least one first object and the at least one second object are selected based on a position of the first collection device relative to the second collection device, such that a scaling factor of
      (A) the position of the first collection device relative to the second collection device versus
      (B) the position of the first object relative to the second object in the sample preparation is a scaling factor (A:B) greater than one, thereby microdissecting the sample preparation.

2. The method according to claim 1, further comprising, subjecting the sample preparation to laser irradiation thereby detaching and transporting a third object from the sample preparation to a third object collection device, the third object being transported such that the position of the third collection device relative to the first collection device is substantially equal to the position of the third object relative to the first object in the preparation multiplied by the scaling factor.

3. The method according to claim 1, further comprising ascertaining a position of the second collection device relative to the first collection device and then selecting at least one of the first and second objects to be transported based upon the ascertained position.

4. The method according to claim 3, further comprising recording an overview image of at least one segment of the sample preparation; from the image, selecting a region therein of the sample preparation; and then selecting the first and second objects in the sample preparation to be detached and transported from within the preparation region.

5. The method according to claim 4, further comprising carrying out the first and second object-selecting step by: ascertaining the number of the collection devices disposed along an axis defined by the first and second collection devices; ascertaining a length of the sample preparation region in a direction parallel to the axis; and determining a position of the second object relative to the first object by multiplying by an integer a ratio of the ascertained length of the preparation region to the ascertained number of collection devices.

6. The method according to claim 5, wherein the integer is equal to the number of collection devices disposed along the axis between the first and the second collection devices plus 1.

7. The method according to claim 1, further comprising ascertaining a thickness of the sample preparation in a vicinity of each of the first and second objects; and selecting the first and second objects so that in the respective areas of the first and second objects each object is selected and irradiated according to the thickness of the preparation respectively ascertained in the vicinity of the first and second objects.

8. The method according to claim 7, further comprising ascertaining the thickness of the preparation in the vicinity of the first and second objects by digital holographic interferometry.

9. The method according to claim 1, wherein in step (c) the detaching comprises cutting the preparation and the transporting comprises accelerating the first and second objects by the laser irradiation.

10. The method according to claim 1, wherein the sample preparation is a biological sample preparation.

11. The method according to claim 1, wherein the sample preparation comprises a tissue section.

12. The method according to claim 1, wherein the sample preparation comprises a cell culture.

13. The method according to claim 1, further comprising providing a plurality of secondary collection devices for collecting secondary objects detached from the sample preparation, the plurality of secondary collection devices having a predefined spatial configuration relative to one another; transporting a first secondary object of the preparation to a first secondary collection device and transporting a second secondary object of the preparation to a second secondary collection device, respectively, by laser irradiation, at least one of the first secondary and second secondary objects being transported respectively to the first secondary and second secondary collection devices so that a position of the second secondary collection device relative to the first secondary collection device corresponds to a position of the second secondary object relative to the first secondary object in the preparation, the first secondary object being in a vicinity of the first object in the preparation and the second secondary object being in a vicinity of the second object in the preparation, wherein the first and second secondary objects are different from the first and second objects.

14. The method according to claim 1, wherein the first and second collection devices are respectively a first and a second well of a microtitre plate.

15. The method according to claim 1, wherein the first and second collection devices each are selected from the group consisting of a segment of a uncoated planar carrier and a segment of an adhesive-coated planar carrier.

16. A method for performing microdissection, the method comprising:
  a. providing a sample preparation, the sample optionally comprising biological material;
  b. providing a plurality of means for collecting objects detachable from the sample preparation, the plurality of means positioned in a spatial configuration relative to one another and a distance from the sample preparation sufficient for spatial and selective collection of a plurality of the objects when the objects are detached from the sample preparation; and
  c. subjecting the sample preparation to laser irradiation thereby detaching and transporting:
    i. a first object from the sample preparation to a first object collection means and
    ii. a second object from the preparation different from the first object to a second object collection means,
  wherein at least one of the first object of the preparation and the second object of the preparation being selected based on a position of the first collection means relative to the second collection means, such that a scaling factor of
    (A) the position of the first collection means relative to the second collection means versus
    (B) the position of the first object relative to the second object in the sample preparation is a scaling factor (A:B) greater than one, thereby microdissecting the sample preparation.

* * * * *